United States Patent [19]

Uchida

[11] Patent Number: 4,893,515

[45] Date of Patent: Jan. 16, 1990

[54] SAMPLE-SUCKING CONDITION CHECKING METHOD AND SYSTEM

[75] Inventor: Makoto Uchida, Ootawara, Japan

[73] Assignee: Kabushiki Kaisha Toshiba, Kawasaki, Japan

[21] Appl. No.: 287,553

[22] Filed: Dec. 20, 1988

Related U.S. Application Data

[63] Continuation of Ser. No. 94,878, Sep. 10, 1987, abandoned.

[30] Foreign Application Priority Data

Sep. 18, 1986 [JP] Japan .................................. 61-218006

[51] Int. Cl.$^4$ ............................................. G01N 1/14
[52] U.S. Cl. .................................................. 73/864.34
[58] Field of Search ................ 73/863, 863.01, 863.02, 73/863.03, 864.34, 864.73, 863.83, 864.11–864.18, 864.21–864.25; 422/100

[56] References Cited

U.S. PATENT DOCUMENTS 4,675,301 6/1987 Charneski et al. ............... 73/863.01

Primary Examiner—Robert R. Raevis
Attorney, Agent, or Firm—Oblon, Spivak, McClelland, Maier & Neustadt

[57] ABSTRACT

In order to check a sample sucking condition at the sampling nozzle, minimum and maximum pressure values in normal sample sucking condition, and a judging value used in a formula for determining the sample sucking condition are preset. A pressure level before the start of the sample suction, a pressure level during the sample suction, and a pressure level immediately before the completion of the sample suction is measured. A clogged condition is detected during the sample suction. A normal condition and a no-sample condition are determined after the sample suction.

8 Claims, 5 Drawing Sheets

SAMPLE-SUCKING CONDITION CHECKING METHOD AND SYSTEM

This application is a continuation of application Ser. No. 094,878, filed on Sept. 10, 1987, now abandoned.

BACKGROUND OF THE INVENTION

This invention relates to a sample-sucking condition checking method and system which, incorporated in an apparatus for sucking a liquid-like sample such as a serum, for automatic chemical analysis, judges the sample-sucking condition thereof by monitoring the suction pressure.

Conventionally, an automatic apparatus used, for example, for chemical analysis, is equipped with a device which monitors the sample sucking condition thereof by use of a high-sensitivity pressure sensor. Specifically, this sensor detects any variation in suction pressure upon sucking of the sample. The suction pressure value output from the pressure sensor indicates a given value when a viscosity of the sample to be sucked is within a normal value range and when a proper sucking operation is performed. If the forward end of a sampling nozzle is clogged with, for example fibrin, a suction pressure, greater than a suction pressure within the normal range will be indicated, whereby the clogged condition will then be determined. Where, on the other hand, the sample is not present before the start of the sample suction or during the sample suction pressure will become smaller than suction pressure within the normal range, and thus, the sample sucking condition will be judged as "no sample" condition.

In the conventional device adapted to monitor the suction conditions of the sample, the suction pressure is detected during sample-suction, to thereby obtain a data value which is then analog/digital (A/D)-converted into digital data for recording. After the completion of suction, the suction pressure waveform is analyzed and, in accordance with the suction condition, judged as indicating a "normal", a "clogged", or a "no sample" condition.

Since, however, according to this method, the performing of a proper sample-sucking procedure is delayed, particularly when the "clogged" condition is indicated, the pressure sensor is then subjected to a large pressure, with the risk that it will be damaged, as a result. Thus an conventional system has to judge the suction condition after all the suction pressure values have been collected and recorded.

It is now generally felt desirable that in order that the suction condition, at the time of sample suction, can be judged readily and rapidly, a simpler system should be implemented therefor, that the "clogged" condition be detected earlier, in order to reduce the risk of the pressure sensor being damaged, and that the sample-sucking condition be judged irrespective of, for instance, sample type and sampling tube diameter.

SUMMARY OF THE INVENTION

Accordingly it is the object of this invention to provide a sample-sucking condition checking method and system which can be used in, for example, a chemical analyzing apparatus, and which can check the sample-sucking condition by monitoring the sucking pressure by means of a pressure sensor.

A sample-sucking condition checking method according to the present invention comprises the steps of:

(a) measuring the suction pressure at a sampling nozzle, before suction of a sample starts;

(b) starting suction of the sample by driving a sampling pump;

(c) measuring the suction pressure level at the sampling nozzle, at the time when the suction speed of the sampling pump reaches a maximum level during suction of the sample;

(d) determining, on the basis of the pressure level measured, whether or not a clogged condition exists at said sampling nozzle;

(e) stopping the sampling pump if a clogged condition exists at said sampling nozzle;

(f) measuring, if no clogged condition exists at said sampling nozzle, the suction pressure level at the sampling nozzle, at the time when the suction speed of the sampling pump reaches a middle level, immediately before the completion of sample-suction; and (g) determining the sample-sucking condition, by use of three kinds of pressure levels, after suction of the sample has been completed.

The present invention additionally provides a sample-sucking condition checking system, which comprises:

means for measuring the pressure at a sampling nozzle, before suction of a sample starts;

means for starting suction of said sample by driving a sampling pump;

means for measuring the pressure level at the time when the suction speed of the sampling pump reaches a maximum during suction of the sample;

means for determining, on the basis of the pressure level measured, whether or not a clogged condition exists at said sampling nozzle;

means for stopping the sampling pump if clogged condition exists at said sampling nozzle;

means for measuring, if no sample condition exists at said sampling nozzle, the pressure level at said sampling nozzle, at the time when the suction speed of the sampling pump reaches a middle level, immediately before the completion of sample-suction; and means for determining the sample-sucking condition, by use of three kinds of pressure levels, after suction of the sample has been completed.

DETAILED DESCRIPTION OF THE PREFERRED EMBODIMENT

A sample sucking condition checking system according to the embodiment of the invention will be explained below with reference to the accompanying drawings.

Figure 1:
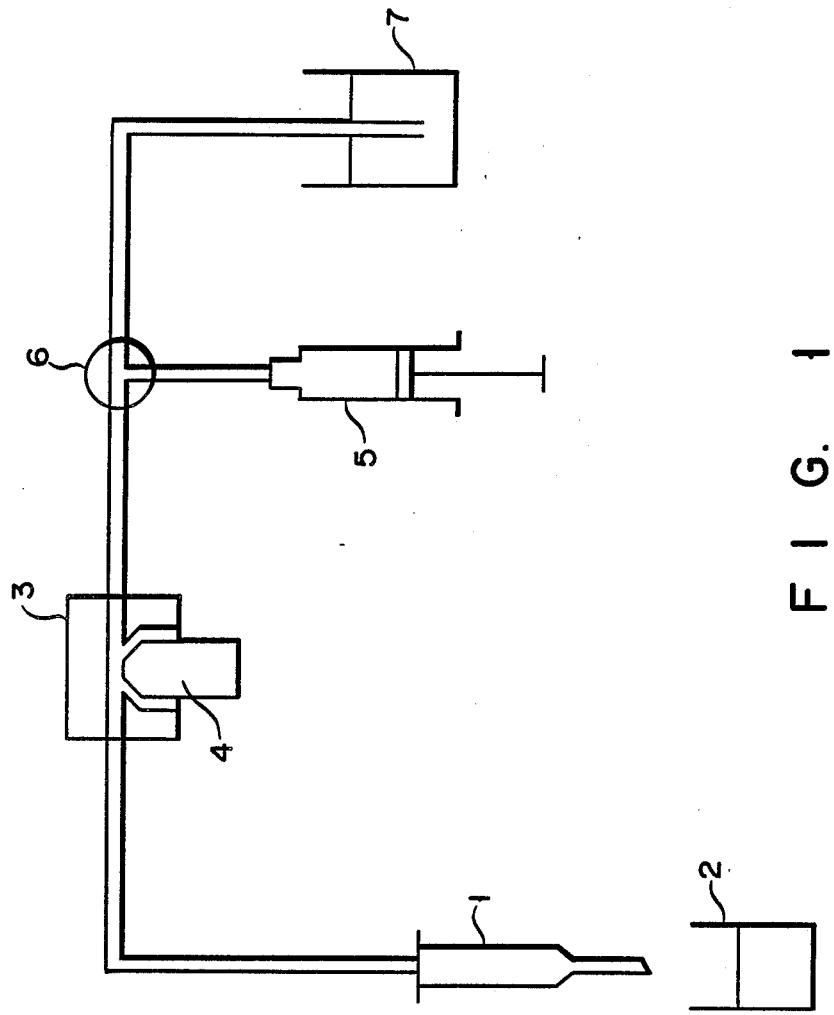
FIG. 1 is a diagram showing a sample-sucking apparatus to which the present invention is applied.

FIG. 1 shows an arrangement of a sample suction apparatus for carrying out this invention. In FIG. 1, sampling nozzle 1 is adapted to suck a sample contained in sampling cup 2 and a tube coupled to sampling nozzle 1 is coupled to piezoelectric transducer-equipped pressure sensor 4 at the location of three-way joint 3. A tube extending from three-way joint 3 is coupled via three-way cock 6 to sampling pump 5 and to water supply cup 7. Water supply cup 7 is adapted to cause the tube channel to be occupied with water up to and near sampling nozzle 1 before the sample is sucked. That water is employed as a washing liquid.

Figure 2:
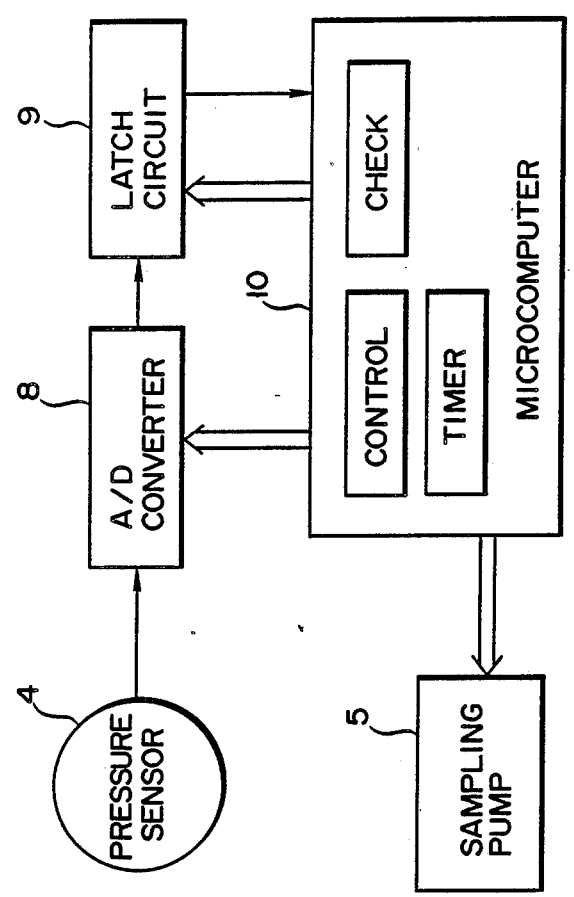
FIG. 2 is a block diagram showing a sample sucking condition checking system according to one embodiment of the present invention.
Figure 4:
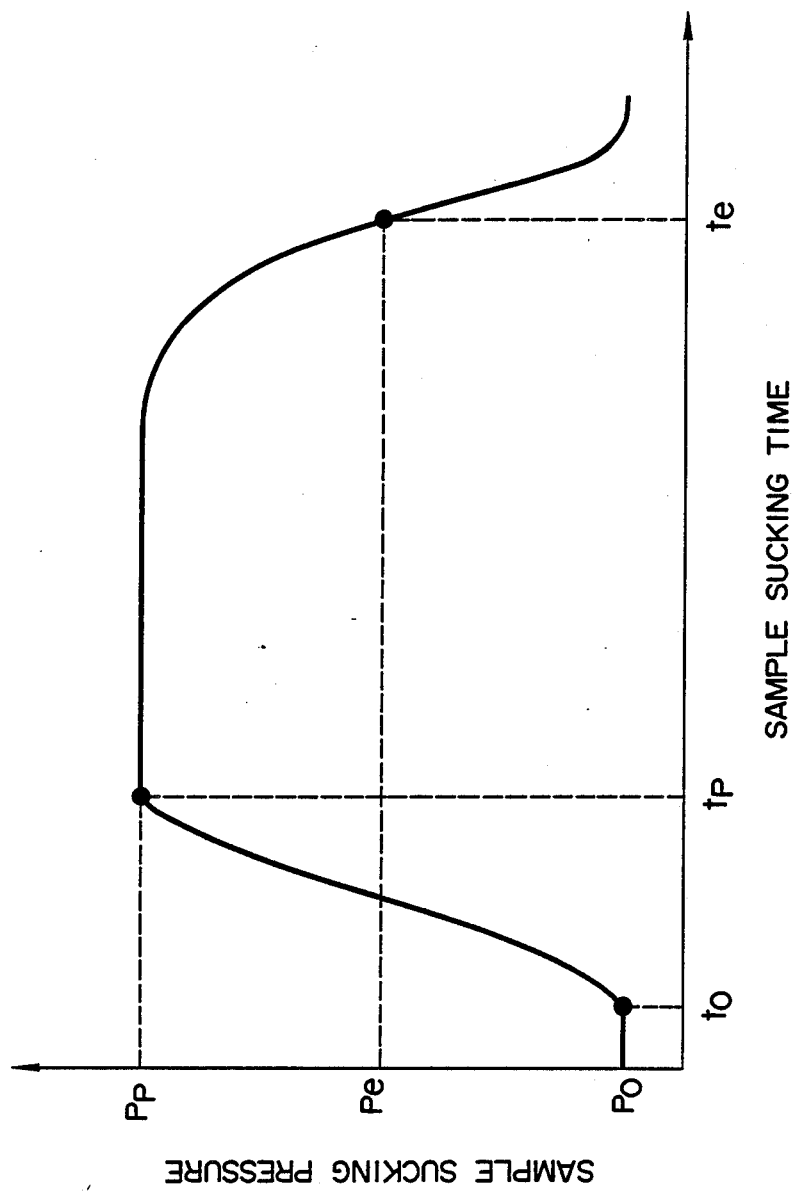
FIG. 4 is a graph illustrating how the sample-sucking pressure changes with time.

FIG. 2 is a block diagram showing an arrangement of a system for checking the suction condition of a sample with the use of a pressure detected by pressure sensor 4. In the block diagram shown in FIG. 2, microcomputer 10 has the functions as a control circuit, judging circuit and timer circuit. A pressure which is involved upon the suction of a sample is detected with the use of pressure sensor 4 and translated into an electric signal. Then the electric signal is A/D converted to digital data on the basis of a timing clock from microcomputer 10. Of the output of A/D converter 8, a value Po before the start of sample suction, value Pp under the suction condition and value Pe immediately before the completion of the sample suction are latched by latch circuit 9 at the latch timing of microcomputer 10 as shown in FIG. 4. Microcomputer 10 judges the sample sucking condition on the basis of three kinds of values, that is, Po, Pp and Pe and forms judgment in accordance with the following judging equations:

(1) For the "normal" condition $$P_L \leq P_P \leq P_H \text{ and } \gamma = (Pe - Po)/(Pp - Po) > C;$$

(2) for the "no sample" condition $$P_P < P_L \text{ or } \gamma = (Pe - Po)/(Pp - Po) \leq C;$$

and (3) for the "clogged" condition $$P_P > P_H$$

where $P_H$: a maximum acceptable pressure level at the time of the normal suction of the sample;
$P_L$: the minimum acceptable pressure level; and
$\gamma$: a ratio of the value Pe involved immediately before the completion of the suction of a sample with the value Po, before the start of the sample suction, set as a reference and the value Pp under the suction of the sample.

A judging value C employed in the aforementioned equation should be altered if there is a great variation among samples in terms of the viscosity, etc., and in general is obtained experimentally.

Microcomputer 10 has various functions, for example, the driving of sampling pump 5, the setting of the latch timing of latch circuit 9, and the stopping of sampling pump 5 when microcomputer 10 judges the sample suction condition as "clogged".

Figure 3A:
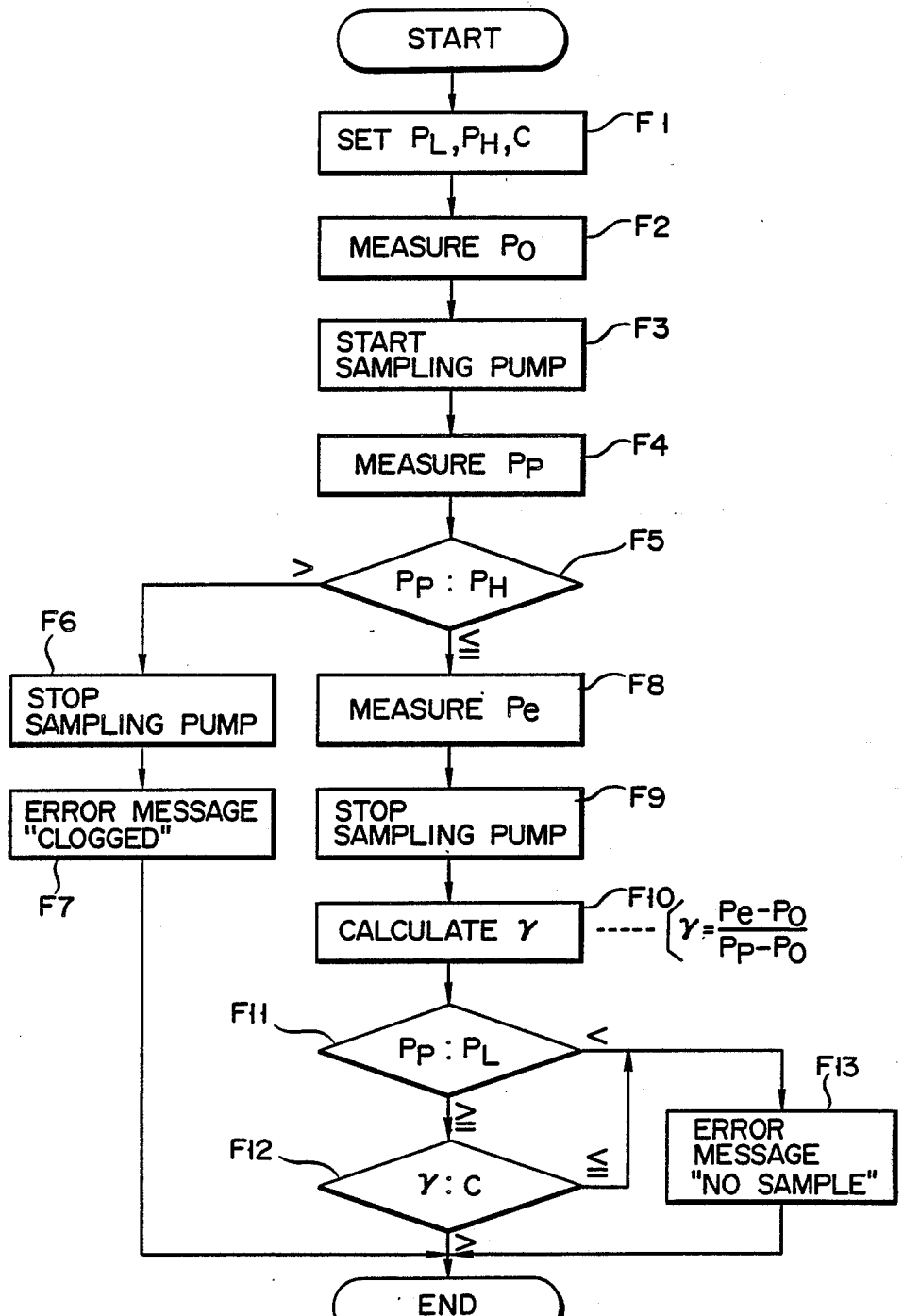
FIGS. 3A and 3B are flow charts explaining the method of checking the sample sucking condition.

The procedure of judging the sucking condition of the sample through the use of the microcomputer of the sample sucking condition checking system will be explained in accordance with the flow chart shown in FIG. 3A.

When a program for judging the aforementioned sample sucking condition is run, then the acceptable minimum pressure value $P_L$, the maximum acceptable pressure value $P_H$ and judging value C in the equation $\gamma$ of judging the sample sucking condition are set to microcomputer 10 (step F1). At step F2, the value Po before the start of the sample suction is measured. At step F3 sampling pump 5 is started and, at the same time, microcomputer 10 commences a time count from the start of the sample suction and measures a value Pp, an initially measured value at which the suction speed of sampling pump 5 becomes maximum level during the suction of the sample (step F4).

At step F5, the value Pp actually measured at step F4 is compared with the preset maximum $P_H$ and, if the value Pp obtained is greater than a maximum acceptable pressure value $P_H$, the microcomputer 10 judges this condition as "clogged", stopping sampling pump 5 (step F6). An error message is displayed, indicating the "clogged" condition (step F7).

If at step F5 the value Pp actually measured at step F4 is not greater than the maximum acceptable pressure value $P_H$, the microcomputer 10 judges this condition as being "no clogged" condition and measures a value Pe at a time (step F8) when the suction pressure by sampling pump 5 reaches a middle level between the pressure values $P_o$ and $P_p$ in the plot of FIG. 4, stopping sampling pump 5 (step F9).

At step F10, the equation $\gamma = (Pe - Po)/(Pp - Po)$ is calculated with the use of the aforementioned three kinds of values Po, Pp and Pe. At step F11, the value Pp actually measured is compared with the initially predetermined minimum acceptable pressure value $P_L$ and, if the value Pp obtained is smaller than the minimum acceptable pressure value $P_L$, the microcomputer 10 judges this condition as being "no sample" condition, displaying an error message representing the "no sample" condition (step F13).

If, in step 11, the value Pp obtained is not smaller than the minimum acceptable pressure value $P_L$, comparison is made (step F12) between the judging value C initially determined and the value of the judging equation $\gamma$ calculated at step F10. Where the value of the judging equation $\gamma$ is greater than the judging value C, the microcomputer 10 judges this condition as being "normal" condition. Where, on the other hand, the value of the judging equation $\gamma$ is not greater than the judging value C, the microcomputer 10 judges this condition as being "no sample" condition and carries out the corresponding processing at step F13.

The aforementioned judging operation is performed until the suction of all the sample is completed.

Figure 3B:
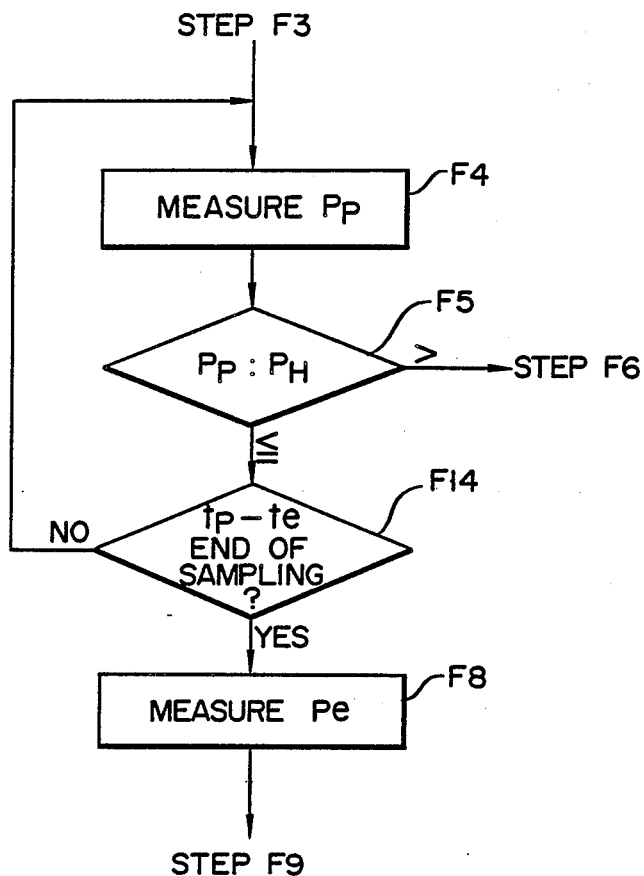

Since the amount of sample sucked varies depending upon the number of items for which checking is made, there is a corresponding variation in the time interval between the time tp when the suction speed of the sampling pump reaches a maximum level during the suction of the sample and the time te when the suction speed of the sampling pump reaches a middle level immediately before the completion of the sample suction. The "clogged" condition usually occurs at the time interval from the time when the sample suction is started to the time tp when the suction speed of the sampling pump reaches a maximum level during the suction of the sample. Where the "clogged" condition occurs during the time interval from the time tp when the suction speed of the sampling pump reaches the maximum level during the suction of the sample to the time te when the suction speed reaches the middle level immediately before the completion of the suction of the sample, if the time interval involved is long, a great load is inflicted on the pressure sensor, causing a damage to the pressure sensor. In order to avoid this, it is only necessary to add the processing function of, while the suction pressure involved at the aforementioned time interval is sampled at a proper sampling time, monitoring the sucking condition. Stated in more detail, step F14 is provided subsequent to step F5 of FIG. 3A as shown in FIG. 3B to provide a loop for sampling the suction pressure at a given sampling time. In this way it is possible to rapidly cope with any "clogged" condition as involved at the aforementioned time interval.

The operation of this embodiment will be set forth below.

First, the pressure before the start of the sample suction is detected by pressure sensor 4 and the forward end portion of sampling nozzle 1 is inserted into sampling cup 2. The output of pressure sensor 4 is A/D converted to digital data which in turn is latched to latch circuit 9 at the latch timing of microcomputer 10 and then delivered to microcomputer 10.

Then sampling pump 5 is driven by microcomputer 10, starting the suction of the sample by sampling nozzle 1. According to this invention the pressure involved is detected by pressure sensor 4 during the suction of the sample to produce an electric signal. The electric signal is A/D converted to digital data.

Microcomputer 10 has the function of making time count from the start of the sample suction. As shown in FIG. 4, a latch timing signal is produced at times tp and te each passed predetermined periods from the start of the sample suction.

Not only the value Po before the start of the sample suction, but also the value Pp at the time tp when the suction speed of the sampling pump reaches a maximum level during the suction of the sample and the value Pe at the time te when the suction speed of the sampling pump reaches a middle level before the completion of the sample suction, is latched to latch circuit 9. The output of the latch circuit is delivered to microcomputer 10. At the time the aforementioned value Pp is input, microcomputer 10 checks to see whether or not any "clogged" condition is involved. If the microcomputer 10 judges that condition as being "clogged", the result of judgement is delivered as an output to the judging circuit and microcomputer 10 is allowed to be interrupted, stopping sampling pump 5. In this way the "clogged" condition as shown in (3) is earlier detected so that a suitable procedure may be carried out. As a result, it is possible to prevent pressure sensor 4 from being damaged by a large pressure involved.

Microcomputer 10 judges the conditions (1) and (2) after the three kinds of values are all input. In this connection it is to be noted that it is not always necessary to judge all the conditions (1) and (2), that is, it is only necessary to judge the "no sample" condition or the "normal" condition through the use of the judging equation $\gamma$.

Since the judging equation given by $$(P_e - P_o)/(P_p - P_o)$$

reflects the pressure condition irrespective of the kind and quantity of the sample as well as the diameter of the sampling nozzle and tube, etc., accurate judgement can be made even if the aforementioned conditions are altered. The judgment of the pressure condition is made based only on the three kinds of values as set forth above and, for this reason, the system can be simplified in comparison with the conventional counterpart for judging the suction condition after all the have been detected during the suction of the sample.

This invention is not restricted to the aforementioned embodiment only and modified in a variety of ways without departing from the spirit and scope of this invention.

What is claimed is:

1. A sample-sucking condition checking method comprising the steps of:
    (a) measuring a first suction pressure value $P_o$ at a sampling nozzle, before suction of a sample starts;
    (b) starting suction of the sample by driving a sampling pump;
    (c) measuring a second suction pressure value $P_p$ at the sampling nozzle when the suction speed of the sampling pump reaches a maximum level during the suction of the sample;
    (d) comparing the second suction pressure value $P_p$ with a maximum acceptable pressure value $P_H$ to determine whether or not a clogged condition exists at the sampling nozzle;
    (e) stopping the sampling pump if the clogged condition exists at said sampling nozzle;
    (f) measuring, if no clogged condition exists at the sampling nozzle, a third suction pressure value $P_e$ at the sampling nozzle when the suction speed of the sampling pump reaches a middle level before the completion of sample-suction; and
    (g) comparing a first change between the first suction pressure value $P_o$ and the second suction pressure value $P_p$ with a second change between the first suction pressure value $P_o$ and the third suction pressure value $P_e$ to determine whether or not the sample-suction is normal.

2. The method according to claim 1, wherein the clogged condition includes:

$$P_p > P_H,$$

wherein
    $P_p$: the second suction pressure value when the suction speed of the sampling pump reaches a maximum level during sample-suction;
    $P_H$: the maximum acceptable pressure value during normal suction of the sample.

3. The method according to claim 1, wherein the sample-sucking condition includes:

(1) $P_L \leq P_p \leq P_H$ and $\gamma = (P_e - P_o)/(P_p - P_o) > C$ for a normal condition; and (2) $P_p < P_L$ or $\gamma = (P_e - P_o)/(P_p - P_o) \leq C$ for a no-sample condition.

where
    $P_H$: the maximum acceptable pressure value during normal suction of the sample;
    $P_L$: the minimum acceptable pressure value during normal suction of the sample;
    $P_o$: the first suction pressure value before start of sample-suction;
    $P_e$: the third suction pressure value when the suction speed of the sampling pump reaches a middle level before the completion of sample-suction;
    $P_p$: the second suction pressure value when the suction speed of the sampling pump reaches a maximum level during sample-suction;
    C: a determination value obtained experimentally.

4. The method according to claim 1, wherein a latch timing at the first, second and third suction pressure values is determined by measuring periods of time from the start of sample-suction.

5. The method according to claim 1, wherein the determination of whether or not the clogged condition exists is performed by detecting a plurality of second suction pressure values during the sample-suction.

6. A sample-sucking condition checking system comprising:
sampling nozzle to be immersed into a sample;
sampling pump connected to the sampling nozzle through a tube for sucking the sample;
pressure sensing means for measuring a first suction pressure value $P_o$ at the sampling nozzle before suction of the sample starts, a second suction pressure value $P_p$ at the sampling nozzle when the suction speed of the sampling pump reaches a maximum level during the suction of the sample, and a third suction pressure value $P_e$ at the sampling nozzle when the suction speed of the sampling pump reaches a middle level before completion of suction of the sample; and
comparing means for comparing a first change between the first suction pressure value $P_o$ and the second suction value $P_p$ with a second change between the first suction pressure value $P_e$ and the third suction pressure value $P_o$ to determine whether or not sample-sucking condition is normal.

7. The system according to claim 6, wherein the sample-sucking condition includes:

(1) $P_L \leqq P_p \leqq P_H$ and $\gamma=(P_e-P_o)/(P_p-P_o)>C$ for a normal condition; and (2) $P_p<P_L$ or $\gamma=(P_e-P_o)/(P_p-P_o)\leqq C$ for a no-sample condition.

(3) $P_p \geqq P_H$
for a clogged condition,
where
$P_H$: the maximum acceptable pressure value during normal suction of the sample;
$P_L$: the minimum acceptable pressure value during normal suction of the sample;
$P_o$: the first suction pressure value before start of sample-suction;
$P_e$: the third suction pressure value when the suction speed of the sampling pump reaches a middle level before the completion of sample-suction;
$P_p$: the second suction pressure value when the suction speed of the sampling pump reaches a maximum level during sample-suction;
C: a determination value obtained experimentally.

8. The system according to claim 6, wherein the pressure sensing means includes microcomputer means for determining a latch timing at the first, second and third suction pressure values by measuring periods of time from the start of sample-suction.

* * * * *